US00PP24918P2

(12) United States Plant Patent
Ault et al.

(10) Patent No.: US PP24,918 P2
(45) Date of Patent: Sep. 23, 2014

(54) ***PHLOX* PLANT NAMED 'FOREVER PINK'**

(50) Latin Name: ***Phlox* hybrid**
Varietal Denomination: Forever Pink

(71) Applicants: James R. Ault, Libertyville, IL (US); Catherine S. Thomas, Northfield, IL (US)

(72) Inventors: James R. Ault, Libertyville, IL (US); Catherine S. Thomas, Northfield, IL (US)

(73) Assignee: Chicagoland Grows, Inc., Glencoe, IL (US)

( * ) Notice: Subject to any disclaimer, the term of this patent is extended or adjusted under 35 U.S.C. 154(b) by 0 days.

(21) Appl. No.: 13/694,646

(22) Filed: Dec. 20, 2012

(51) Int. Cl.
*A01H 5/00* (2006.01)

(52) U.S. Cl.
USPC ..... Plt./320

(58) Field of Classification Search
USPC ..... Plt./320
See application file for complete search history.

*Primary Examiner* — Anne Grunberg
(74) *Attorney, Agent, or Firm* — Penny J. Aguirre

(57) ABSTRACT

A new cultivar of *Phlox*, 'Forever Pink', characterized by its purplish pink flowers that are about 2.5 cm in diameter with the coloration uniform throughout the petals or with a very faint lighter eye, its heavy bloom with almost compete coverage of the plant for three weeks in June in northern Illinois and followed by repeat bloom that covers up of 15% of the plant until late October, its sterility, its strong stems that do not lodge, its compact plant habit, and its high level of resistance to powdery mildew.

2 Drawing Sheets

Botanical classification: *Phlox* hybrid.
Cultivar designation: 'Forever Pink'.

BACKGROUND OF THE INVENTION

The present invention relates to a new and distinct cultivar of *Phlox* plant, botanically of hybrid origin and known as *Phlox* 'Forever Pink' and will be referred to hereafter by its cultivar name, 'Forever Pink'. The new cultivar represents a new herbaceous perennial grown for landscape use.

The new invention arose from an ongoing controlled breeding program by the Inventors in Glencoe, Ill. The objectives of the breeding program are to develop interspecific hybrids of the genus *Phlox* that are well adapted to the climate and soils of the upper Midwest region of the United States.

'Forever Pink' was derived from a cross made in June of 2007 under controlled conditions (that excluded natural pollinators) between an unnamed plant of *Phlox glaberrima* ssp. *triflora* as the female parent and *Phlox* 'Bill Baker' (not patented) as the male parent. The resulting seedlings were planted for evaluation in 2008. 'Forever Pink' was selected in June of 2009 as a single unique plant amongst the resulting seedlings.

Asexual propagation of the new cultivar was first accomplished by stem cuttings by one of the Inventors in October of 2009 in Glencoe, Ill. Propagation by stem cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Forever Pink' as a unique cultivar of *Phlox*.

1. 'Forever Pink' exhibits purplish pink flowers that are about 2.5 cm in diameter; the coloration is uniform throughout the petals or with a very faint lighter eye.
2. 'Forever Pink' blooms heavily with almost compete coverage of the plant for three weeks in June in northern Illinois, followed by repeat bloom that covers up of 15% of the plant until late October (total bloom time of about 21 weeks).
3. 'Forever Pink' has been observed to be sterile, seed is not produced.
4. 'Forever Pink' exhibits strong stems that do not lodge.
5. 'Forever Pink' exhibits a compact plant habit; reaching about 41 cm in height in bloom.
6. 'Forever Pink' has been observed to be highly resistant to powdery mildew.

The female parent of 'Forever Pink', an unnamed plant of *Phlox glaberrima* ssp. *triflora*, differs from 'Forever Pink' in having purplish pink flowers with a distinct white eye, in being fertile, in being taller in height, and in having stems with about 75% lodging. The male parent of 'Forever Pink', 'Bill Baker', differs from 'Forever Pink' in having purplish pink flowers with a distinct white eye, in being fertile, in being taller in height, and in having stems with about 50% lodging. 'Forever Pink' can also be most closely compared to the cultivars 'Minnie Pearl' (not patented) and *Phlox glaberrima* 'Morris Berd' (not patented). 'Minnie Pearl' and 'Morris Berd' are similar to 'Forever Pink' in having its peak bloom in June and in showing a high level of resistance to powdery mildew. 'Minnie Pearl' differs from 'Forever Pink' in having white flowers that are larger in diameter (2.8 cm), in blooming a shorter period of time (17 weeks) and in being taller in height in bloom (54 cm). 'Morris Berd' differs from 'Forever Pink' in having purplish pink flowers with a distinct white eye, in blooming a shorter period of time (8 weeks) and in being taller in height in bloom (56 cm).

BRIEF DESCRIPTION OF THE DRAWING

The accompanying colored photographs illustrate the overall appearance and distinct characteristics of the new *Phlox*.

The photographs were taken in June of two year-old plants of 'Forever Pink' as grown in a trial garden in Glencoe, Ill.

Figure 1:
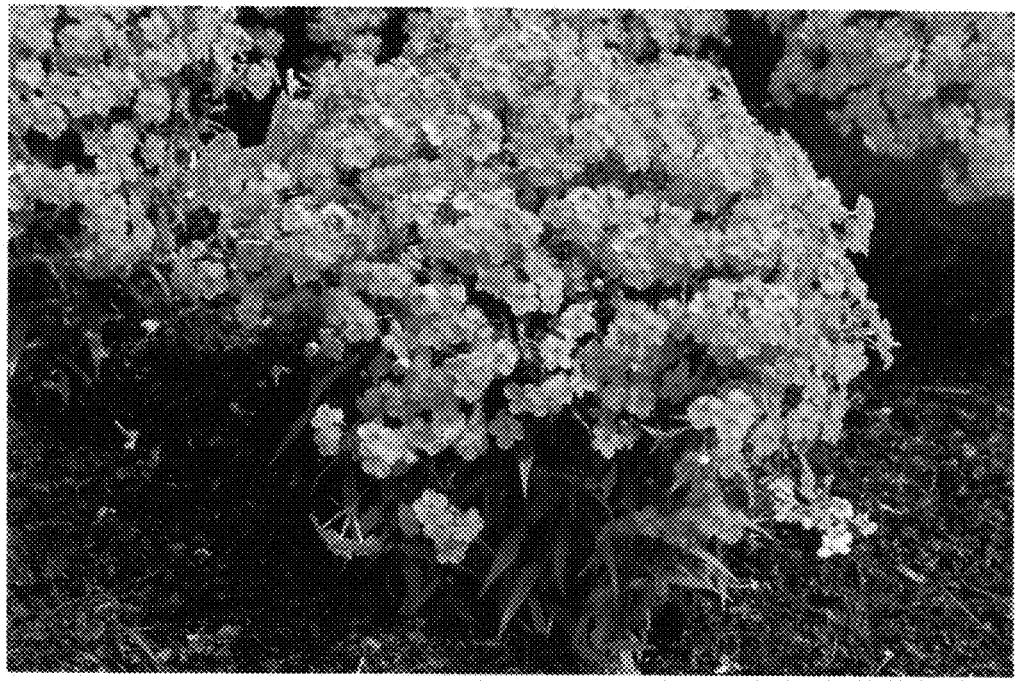

The photograph in FIG. 1 provides a side view of a plant of 'Forever Pink' in bloom.

Figure 2:
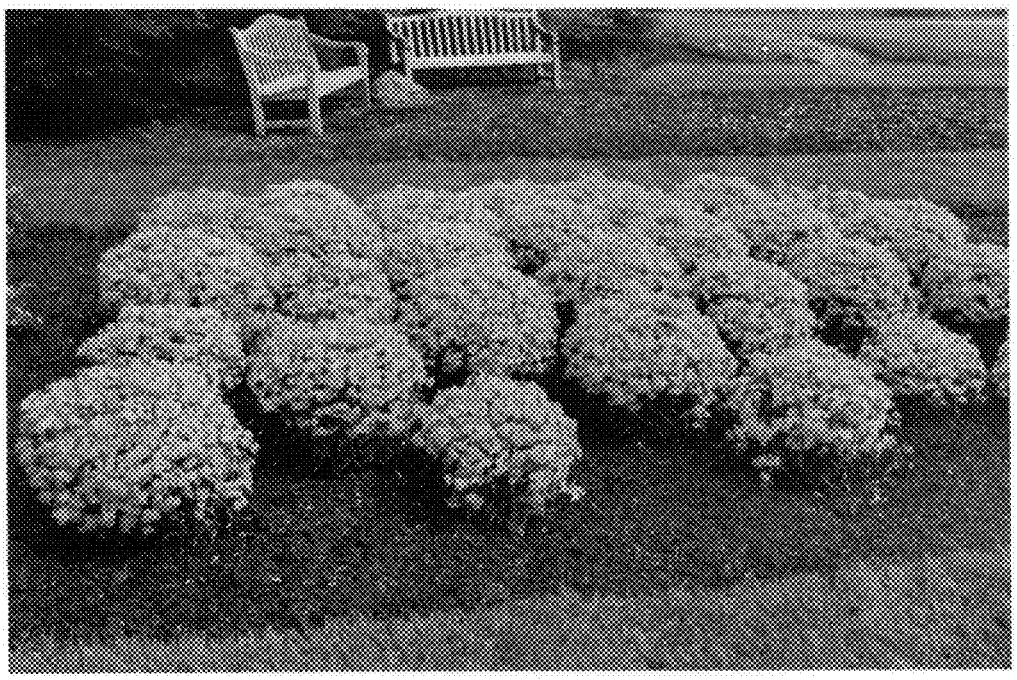

The Photograph in FIG. 2 provides a view of a number of plants of 'Forever Pink' to illustrate its uniform and compact habit.

Figure 3:
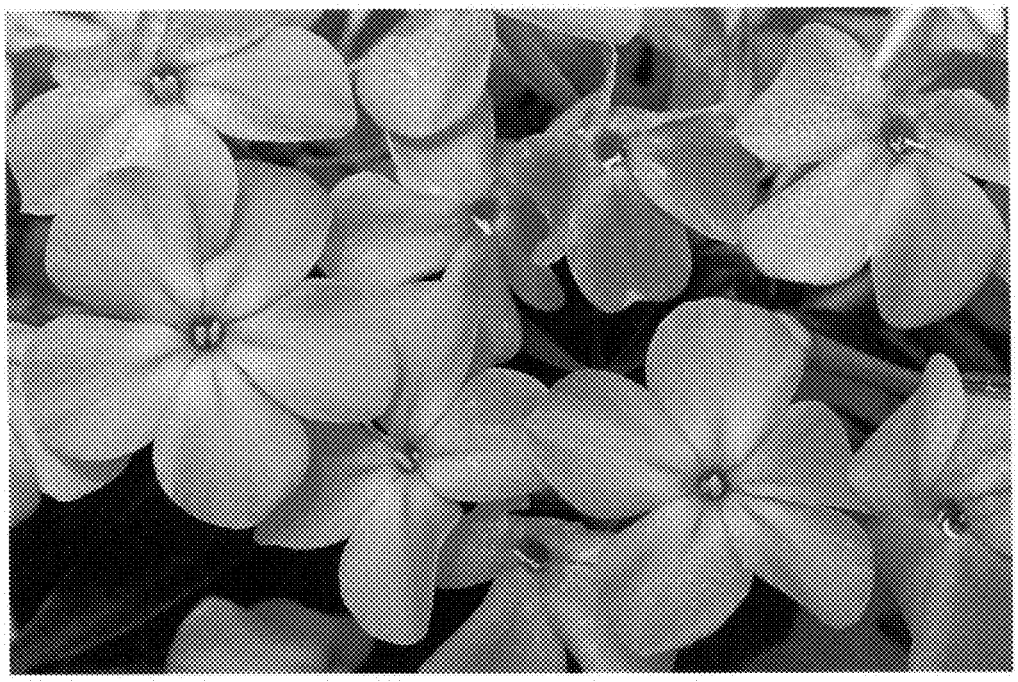

The photograph in FIG. 3 is a close-up view of the flowers of 'Forever Pink'. The colors in the photograph may differ slightly from the color values cited in the detailed botanical description, which accurately describe the colors of the new *Phlox*.

DETAILED BOTANICAL DESCRIPTION OF THE PLANT

The following is a detailed description of two year-old plants of the new cultivar as grown in a trial garden in Glencoe, Ill. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms heavily in June with upwards of 90% of the plant covered in flowers, repeat blooms with up to 15% coverage of blooms until late October in Illinois.

*Plant habit*.—Herbaceous perennial, compact, upright, non-lodging stems.

*Height and spread*.—Reaches about 41 cm in height in bloom (33 cm to top of foliage) and about 47 cm in spread.

*Hardiness*.—At least hardy in U.S.D.A. Zones 4 to 8.

*Diseases and pests*.—Has been shown to be highly resistant to powdery mildew.

*Root description*.—Fibrous.

*Growth rate*.—Vigorous, reaches a mature height in two years from a cutting.

*Propagation*.—Stem cuttings, division is also possible.

Stem description:

*Stem size*.—Main stems, an average of 30 cm in length and 2 mm in width, lateral stems; variable, up to 15 cm in length and 1.5 mm in width.

*Stem shape*.—Oval.

*Stem strength*.—Strong and sturdy, non-lodging.

*Stem color*.—144A and slightly shaded in some areas with 165A.

*Stem surface*.—Glabrous, slightly glossy.

*Stem aspect*.—Held nearly upright.

*Internode length*.—An average of 1.3 cm.

*Branching habit*.—An average of 20 stems per plant one year in age, an average of 3 lateral branches per main stem.

Foliage description:

*Leaf shape*.—Narrowly elliptic.

*Leaf division*.—Simple.

*Leaf base*.—Attenuate.

*Leaf apex*.—Acuminate.

*Leaf venation*.—Pinnate, not conspicuous, matches leaf color on upper and lower surface with very base of mid rib on upper surface 145B.

*Leaf margins*.—Entire.

*Leaf attachment*.—Sessile.

*Leaf arrangement*.—Opposite.

*Leaf surface*.—Glabrous and dull on upper and lower surface.

*Leaf color*.—Upper and lower surface newly formed; 144B, upper surface mature; 137B, lower surface mature; 138B.

*Leaf size*.—An average of 4 cm in length and 9 mm in width.

*Leaf quantity*.—An average of 16 on a stem 10 cm in length.

*Leaf fragrance*.—None.

Flower description:

*Inflorescence type*.—Compound panicle on terminus of main stems and lateral branches.

*Lastingness of inflorescence*.—About 3 to 4 weeks from the opening of the first flower to senescence of last flower, individual flower lasts about 5 days, same characteristics for repeat blooms.

*Inflorescence size*.—An average of 6 cm in height and 7.5 cm in diameter for terminal inflorescences, laterals are smaller with fewer flowers.

*Flower fragrance*.—Faint to moderate, sweet *Phlox* fragrance.

*Flower number*.—Average of 15 per terminal inflorescence, and 5 per lateral stems.

*Flower aspect*.—Upright to outward, dependant on location on the inflorescence.

*Flower bud*.—An average of 3 cm in length and up to 4 mm in width at apex, apex is conical in shape with base linear (tube portion), apex is a blend of 85A and 85B in color, tube portion is a blend of 149D and 85D, calyx portion is a blend of 138B and 138C.

*Flower form*.—Explanate with tubular base.

*Flower size*.—An average of 2 cm in length and 2.5 cm in width.

*Corolla tube*.—About 1.8 cm in length, 2 mm in width, color matches corolla lobe coloration on outer (same as lower surface of lobes) and inner surfaces (same as upper surface of lobes), glabrous and satiny surface.

*Corolla lobes*.—5, orbicular-obovate in shape, held nearly horizontally when fully open, slightly overlapping, about 0.8 cm in length and width, apex rounded, base broadly cuneate and fused to tube, entire margins, upper surface color when opening and mature N78C/D with slight linear marking of N82B near base, lower surface color when first opening and maturing a blend of 85B and 85C, ages to 81C/D on upper surface and 85D on lower surface.

*Calyx*.—Campanulate in form, comprised of fused sepals with lanceolate shaped sepal tips free, an average of 1 cm in length and 3 mm in width.

*Sepals*.—5, primarily fused with free tips, linear in shape, margins entire, base fused (about 80%), apex narrowly apiculate, an average of 1 cm in length and 1 mm in width, inner and outer surface is puberulent, color on upper and lower surface; a blend of 138B and 138C.

*Peduncles*.—Oval in shape, primary an average of 2.3 cm in length and 1.5 mm in width, secondary an average of 1.3 cm in length and 1 mm in width, primary held upright, secondary held at about a 45° angle, glabrous and satiny surface, color 144A and slightly shaded in some areas with 165A, peduncle leaves; an average of 2 pairs, an average of 1.3 cm in length and 3 mm in width, all other characteristics match stem leaf characteristics.

*Pedicels*.—Oval in shape, an average of 3 mm in length and 1 mm in width, glabrous surface, color 144B and slightly shaded in some areas with 165A.

Reproductive organs:

*Gynoecium*.—1 pistil, stigma has 3 branches about 1 mm in length and 145C in color, style is about 1.5 cm in length, very fine and 145C in color, ovary is inferior, oblong in shape, about 2 mm in length and 1 mm in width and 144A in color.

*Androcoecium*.—5 stamens, anthers are basifixed, oblong in shape, 1.5 mm in length and 160C in color, filaments are adnate to petals, 8 mm in length and 145D in color, pollen is abundant in quantity and 17A in color.

*Seeds*.—Plants of the new cultivar have been observed to be sterile (4 years of trials), no seed is produced.

It is claimed:

1. A new and distinct cultivar of *Phlox* plant named 'Forever Pink' as herein illustrated and described.

* * * * *